United States Patent [19]

Pinnow

[11] Patent Number: 4,963,143
[45] Date of Patent: Oct. 16, 1990

[54] LASER SURGICAL APPARATUS WITH A LENSGUIDE

[76] Inventor: Douglas A. Pinnow, Universal Photonics, Inc., 25401 Cabot Rd., Ste. 110, Laguna Hills, Calif. 92653

[21] Appl. No.: 331,751

[22] Filed: Apr. 3, 1989

Related U.S. Application Data

[63] Continuation of Ser. No. 62,589, Jun. 16, 1987, abandoned.

[51] Int. Cl.⁵ .............................................. A61B 17/36
[52] U.S. Cl. ....................................... 604/14; 606/17; 128/395
[58] Field of Search ........................................ 128/4–8, 128/303.1, 395–398; 350/1.1–1.4, 96.26, 319, 504; 606/13–17

[56] References Cited

U.S. PATENT DOCUMENTS

| | | | |
|---|---|---|---|
| 1,864,895 | 6/1932 | Egy | 128/6 |
| 3,466,111 | 9/1969 | Ring | 350/573 |
| 4,148,551 | 4/1979 | MacAnally | 350/54 |
| 4,473,074 | 9/1984 | Vassiliadis | 128/395 |
| 4,641,912 | 2/1987 | Goldenberg | 128/303.1 |
| 4,669,818 | 6/1987 | Myer | 128/398 |

*Primary Examiner*—Max Hindenburg
*Attorney, Agent, or Firm*—Bacon & Thomas

[57] ABSTRACT

A method and apparatus for performing laser surgery by directing infrared and ultraviolet radiant energy from a surgical laser inside a patient's body using a lensguide is disclosed. The lensguide is comprised of a plurality of spaced convex lenses which are disposed within a plurality of rigid tubular segments connected end to end. The lensguide is flexible, allowing it to replace optical fibers in redirecting the radiant energy around bends encountered in surgical applications.

24 Claims, 3 Drawing Sheets

LASER SURGICAL APPARATUS WITH A LENSGUIDE

This application is a continuation of application Ser. No. 07/062,589, filed June 16, 1987, now abandoned.

BACKGROUND OF THE INVENTION

1. Field of the Invention

The invention relates to a method and apparatus for performing laser surgical procedures.

2. Description of Related Art

Contemporary medical practice involves the use of two types of lasers in surgery. One type of laser cuts tissue by applying an intense amount of heat to a small area. Over the past decade three different lasers have emerged as significant for this type of application. They are the argon ion laser that emits in the blue-green portion of the spectrum 0.45 to 0.53 microns, the Nd:YAG laser with its primary emission level at 1.06 and 1.32 microns in the near infrared portion of the spectrum and the $CO_2$ laser that emits at a wavelength of 10.6 microns, well into the infrared portion of the spectrum. Of these three lasers, the $CO_2$ laser has a number of advantages. For example, it is over an order of magnitude more efficient than either the Nd:YAG or the argon ion laser and it has been found to be best suited for cutting tissue.

However, application of the $CO_2$ laser has been hampered by lack of a commercially viable flexible beam delivery means similar to the silica optical fibers that work so well with the Nd:YAG and argon ion lasers. Silica optical fibers are simply not transparent at the 10.6 micron emission wavelength of the $CO_2$ laser. Major efforts in laboratories around the world have been expended to perfect optical fibers of materials that would be suitable for guiding the 10.6 micron beam. Unfortunately, all efforts to date have been frustrated by lack of sufficient transparency, lack of sufficient flexibility, excessive toxicity and/or insufficient lifetime. Other efforts have been placed on making hollow metal or metal clad dielectric waveguides. These guides are very transparent when straight, but their losses increase substantially when the guides are bent to even a modest radius of curvature.

In frustration over the lack of suitable delivery systems for the $CO_2$ laser in surgical applications, it has been proposed to use CO lasers which emit at 5.3 microns rather than 10.6 microns. The shorter wavelength of the CO lasers increases the number of candidate materials that might be selected for optical fiber delivery systems. Although there are more possibilities, there still is no material for transmission at 5.3 microns which gives comparable performance to conventional silica optical fibers at one micron. In addition, at its present state of development, the CO laser is substantially less reliable than current $CO_2$ lasers.

A second type of laser for surgical applications emits ultraviolet radiation at ultraviolet wavelengths which break the chemical bonds of the tissue and converts the tissue directly into gas with very little heating. The lack of heat makes these lasers particularly useful in microsurgical procedures. An example of this type of laser is the excimer laser which typically emits radiant energy at wavelengths in the range of 0.15 to 0.36 microns. Particularly strong emissions can be achieved at 0.193 and 0.248 microns. One of the last hurdles for the excimer laser is finding a suitable flexible delivery medium. Optical absorption in conventional silica optical fibers is too high for procedures that require fibers more than about one foot long. However, to perform a wide variety of surgical procedures requires fibers that are about two meters long.

Before lasers were used for surgical applications, there were a number of different types of endoscopes that were designed so that a surgeon could see inside the human body through a small opening. This was a great aid in diagnosis. The first of these viewing endoscopes was made in a semirigid, tubular structure for straight or almost straight line of sight. These scopes were usually made with an outer thin wall stainless steel tube that contained a number of lenses. Flexibility of these scopes was limited by buckling of the stainless steel tube. As time went on, the need for a more flexible viewing endoscope was recognized. However, rather than extend the semirigid scope technology, the medical field was quick to adopt bundles of silica fibers as the means for obtaining flexible viewing. The bundles have the individual fibers located at the same relative positions at both ends, so that images can be propagated without lenses. This type of assembly, with carefully positioned fibers, is known as a coherent bundle. These bundles worked so well for flexible viewing that there was no motivation for further development of the semirigid endoscope technology to obtain more flexible structures. Unfortunately, as previously described, silica fibers are not satisfactory for transmitting surgical laser beams.

It is, therefore, apparent that there is a need in the art for a flexible delivery medium which is capable of delivering emissions from the two types of lasers used in surgical applications, particularly the infrared emissions from a $CO_2$ laser and ultraviolet emissions from an excimer laser.

SUMMARY OF THE INVENTION

The present invention is directed to a method and apparatus for directing infrared and ultraviolet radiant energy from a surgical laser inside a patient's body for surgery. The invention uses a lensguide comprising a series of equally spaced convex lenses that are secured inside rigid tubular segments that are aligned along a common axis. The ends of each rigid tubular segment are finished so that they fit together tightly, but can be conveniently flexed to a desired curvature. The lensguide directs the infrared and ultraviolet radiant energy from a surgical laser to the desired point in a patient's body with high transparency, even when it is bent to a tight radius of curvature.

The apparatus of the invention comprises, in addition to the lensguide, means adjacent one end of the lensguide for receiving a beam of ultraviolet or infrared radiant energy from a surgical laser at a point outside the patient's body and means adjacant the other end of the lensguide for discharging a beam of ultraviolet or infrared radiant energy from said lensguide to a point at the surface or inside the patient's body for performing the surgical procedure.

The method of the invention comprises emitting a beam of ultraviolet or infrared radiant energy from a surgical laser receiving and directing the beam through the lensguide and discharging the beam from the lensguide at a point inside the patient's body.

Further details of the invention are provided in the detailed description which follows.

BRIEF DESCRIPTION OF THE FIGURES OF DRAWING

FIG. 3b is an expanded view of one segment of the graded index optical fiber shown in FIG. 3a.

FIG. 8 depicts the disposition of the lensguide between a surgical laser and appropriate discharge means.

FIG. 9a depicts the discharge means as a simple transparent window.

FIG. 9b depicts the discharge means as a convex lens.

FIG. 9c depicts the discharge means as a double lens telescope structure.

DETAILED DESCRIPTION OF THE INVENTION

Over the past fifteen years, silica glass optical fiber waveguides have been highly developed, primarily for long distance communication applications in the visible and near infrared portion of the electromagnetic spectrum, to a wavelength of approximately 2 μm. Beyond this wavelength, the attenuation in these fibers rapidly increases making them unusable at the 10.6 μm wavelength of the $CO_2$ laser. For wavelengths in the ultraviolet portion of the electromagnetic spectrum emitted by the excimer laser, optical absorption in conventional silica fibers is too high to make them an acceptable transmission medium.

Figure 1:
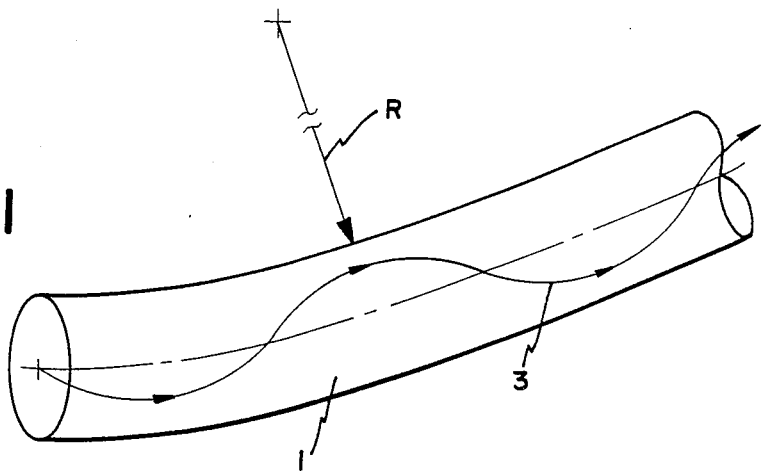
FIG. 1 depicts the path of a ray of light through a typical graded index optical fiber.
Figure 2:
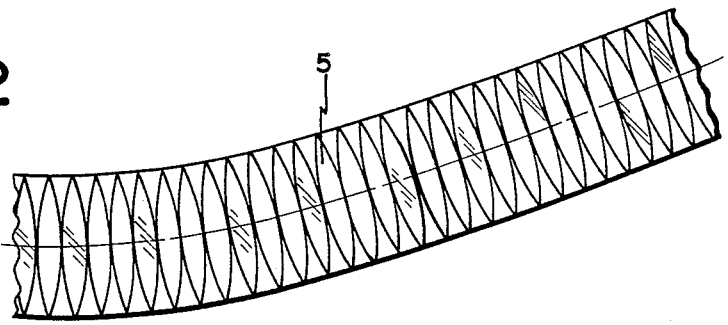
FIG. 2 depicts the discrete lens approximation of a graded index optical fiber.

Even though the silica fibers are not useful for $CO_2$ laser applications, one specific fiber type known as the "graded index" fiber provides a starting point for making a low loss $CO_2$ waveguide. FIG. 1 shows a typical graded index fiber 1 with a parbolic refractive index profile. Also shown in FIG. 1 is a typical path of an optical ray in the graded index fiber 3. It is significant to note that the ray path follows a sinusoidal trajectory about the fiber's axis even when the fiber is bent to a radius of curvature, R. From the viewpoint of optical function, the graded index fiber can be approximated by a series of closely spaced discrete convex lenses 5 such as those shown in FIG. 2.

Figure 3A:
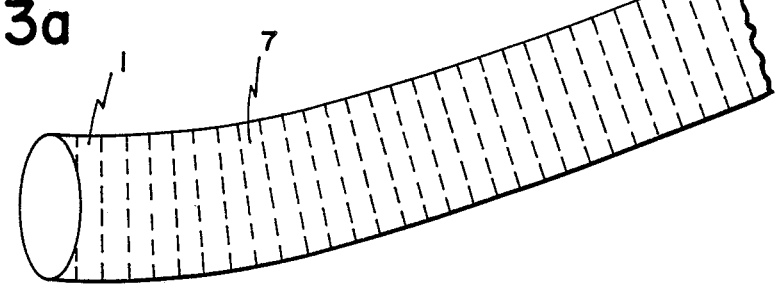
FIG. 3a illustrates the model of a graded index optical fiber as a series of GRIN lenses.
Figure 3B:
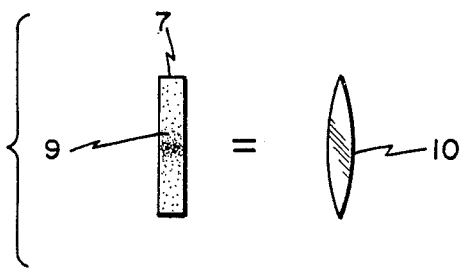

A qualitative explanation for the similarity between a graded index fiber and a series of closely spaced lenses can be made with the aid of FIG. 3. In FIG. 3a the fiber 1 is divided into a series of imaginary slices 7. One particular slice shown in FIG. 3b has a longer optical path length (defined by the product of the physical path length times the index of refraction) at its center 9 than at its edges due to the increasing concentration of higher refractive index constituents going from the edge to the centerline of the slice. The slice from the graded index fiber shown in FIG. 3b is known as a graded index, or GRIN, lens that performs identical to the more conventional convex lens 10 made from a glass of constant composition, which is also shown in this figure for comparison.

Heretofore, there has been little incentive to actually use such a complex structure to substitute for a graded index fiber which works so well in the visible and near infrared region. However, for the ultraviolet and far infrared regions, characteristic of the $CO_2$ and excimer lasers, I have determined that the structure provides the basis for a waveguide under certain conditions.

A rather complete analysis of periodic lens structures for long distance transmission of laser beams through hollow pipes is provided by E.A.J. Marcatili, "Effect of Redirectors, Refocusers, and Mode Filters on Light Transmission Through Aberrated and Misaligned Lenses", *The Bell System Technical Journal*, Vol. XLVI, No. 8, October, 1967. This work was conducted well before low loss optical fibers were recognized as the preferred transmission medium for long distance transmission of laser beams.

Figure 4:
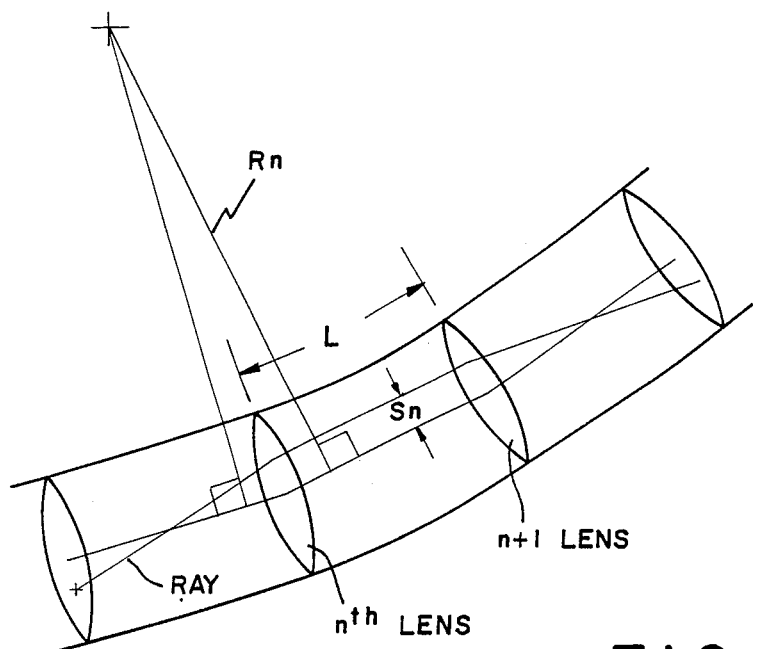
FIG. 4 is an illustration of a periodic lens structure with lenses of focal length f.

Referring to FIG. 4, Marcatili teaches that the (periodic lens) guide is completely defined by the focal length f of the lenses, the lens separation L, and the radius of curvature $R_n$ of the guide at every lens. The beam axis is characterized by the distance $S_n$ to the guide axis at the $n^{th}$ lens. If the beam is launched through the center of the first lens, it is known that $S_n$ is related to L, f and $R_n$ by $$S_n = \frac{L^2}{\sin \theta} \sum_{m=1}^{n-1} \frac{\sin(n-m)\theta}{R_m}$$

where $$\cos \theta = 1 - \frac{L}{2f}.$$

If a laser beam with a Gaussian profile, typical of a $TEM_{oo}$ laser mode, is properly launched into the periodic lensguide, its half width will remain fixed at a value of $$\omega = \frac{\lambda L}{\pi \sin \theta}$$

where λ is the free space laser wavelength. This launching can be achieved by employing a simple or compound convex lens to transform the output beam from laser to the desired "waist" or half width, ω, using well known relationships.

The Marcatili analysis is helpful in designing a lensguide for directing an ultraviolet or infrared emitting laser beam for surgical applications. For purposes of illustration, the $CO_2$ laser with a 10.6 μm emission is selected as an example. The diameter of the lensguide is preferably limited to the range of about 3 to 5 mm so that it can be inserted into the biopsy channel of conventional medical endoscopes, similar to the way optical fibers are presently used to guide the argon ion and Nd:YAG laser beams into the body. The convex lenses are preferably fabricated from ZnSe, which is known for its excellent transmission properties at 10.6 μm. The ZnSe lenses are preferably antireflection coated using standard techniques. Using such lenses, the transmission losses at 10.6 μm are in the range of 0.1% per optical surface.

If the lens spacing is selected to be 1 cm and the focal length of each lens is in the range of 3 to 10 mm, the lensguide can be comfortably bent to a radius of curvature in the range of 5 to 10 cm. This is satisfactory for most internal surgery applications. Table I is a summary of the lensguide characteristics for various diameters and focal lengths.

TABLE I

Performance of a lensguide with segment length L = 1 cm and λ = 10.6 μm

| Guide Number | focal Length f | Maximum displacement of beam axis when bent to a radius of curvature of: 10 cm | 5 cm | Laser beam half width ω | Pitch Length of ray path |
|---|---|---|---|---|---|
| 1 | 3.3 mm | 1 mm | 2 mm | 0.25 mm | 3 cm |
| 2 | 5 mm | 1 mm | 2 mm | 0.27 mm | 4 cm |
| 3 | 10 mm | 2 mm | 4 mm | 0.30 mm | 6 cm |

It can be seen that the lensguide 1 and 2 described in Table I could be constrained to a tube with an inside diameter slightly less than 3mm if it is bent no less than a 10 cm radius of curvature. This follows because the maximum displacement from the centerline plus the beam radius is less than the 1.5 mm radius of the 3mm diameter lensguide. As long as the lensguide does not exceed this radius of curvature there will be very little difference in transmission loss between a straight and curved guide. Alternatively, guides 1 and 2 could be bent as tight as a 5 cm radius of curvature while maintaining low loss if the tube and lenses are enlarged to a 5 mm diameter. This type of performance is far superior to that of the present hollow waveguides which are very sensitive to bending. The range of focal lengths shown in Table I are preferred because the lensguide will fit into existing surgical endoscopes, have excellent flexibility, yet not excessive optical losses. Focal lengths between 2 mm and 20 mm are considered suitable for most all surgical applications. Outside this range the lensguide has insufficient flexibility; excessive diameter or higher attenuation than desired.

The overall transmission loss for a 1 meter length of such a lensguide made with 1 cm segments will be approximately 20% (0.1% per surface times 200 surfaces). This is somewhat superior to the 1dB/meter loss objective set as a target for a practical beam transmission device.

Figure 5:
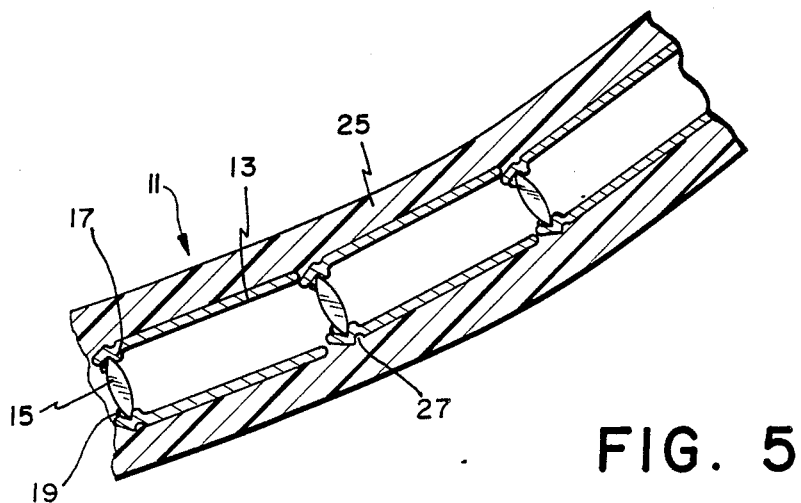
FIG. 5 is a cross sectional view of a lensguide designed in accordance with the invention.

The power handling capability of this type of lensguide is limited by the heat build-up caused primarily by the 0.1% loss per surface of the lenses. A portion of this loss will be due to scattering which is of no major consequence. However, the remaining portion will be absorbed and converted into heat which must be conducted away from the localized spot on the lens where the laser beam passes to limit the local temperature rise. This is necessary to preclude damage to the antireflection coating of the substrate materials. To aid in the conduction of heat for high power applications, the circumference of the lens can be bonded to the internal wall of the tubular segment, as shown in FIG. 5, by glue or some similar medium which will help conduct the heat generated in the lens to the tubular segment.

Such a lensguide could easily handle a 100 watt $CO_2$ laser beam, which is the maximum power presently used in surgical applications. In this case the heat generated in each segment having two optical surfaces will be at most 0.2 watts. While the lensguide will perform quite well using conventional ZnSe lenses for the highest power levels, use of lenses made from a material with a higher thermal conductivity, such as germanium or diamond, may be desirable.

Based on the previously cited analysis by Marcatili, it is desirable to minimize mode conversion due to normally expected aberrations in the lenses. To accomplish this, it is preferred to choose the distance L between lenses such that the period of oscillation of the laser beam (i.e., the pitch length of the ray path given in Table I) does not coincide with an integer number of lens spacings.

It is also apparent that the lensguide could continue to function if there were some variability in the tube lengths, focal lengths, etc. However, the use of identical components and parameters has the advantage of being preferred for large scale or mass production.

FIG. 5 shows a lensguide designed in accordance with the invention. Lensguide 11 is comprised of a series of tubular metal segments 13 with a lens 15 fixed in place at one end of the segment. An internal ridge 17 is provided in the segment at the lens-end to align the lens. A bonding agent 19 is placed on the side of the lens opposite the internal ridge to secure the lens in place in the segment. The bonding agent also helps conduct heat from the lens to the tubular metal segment as previously described.

Figure 6:
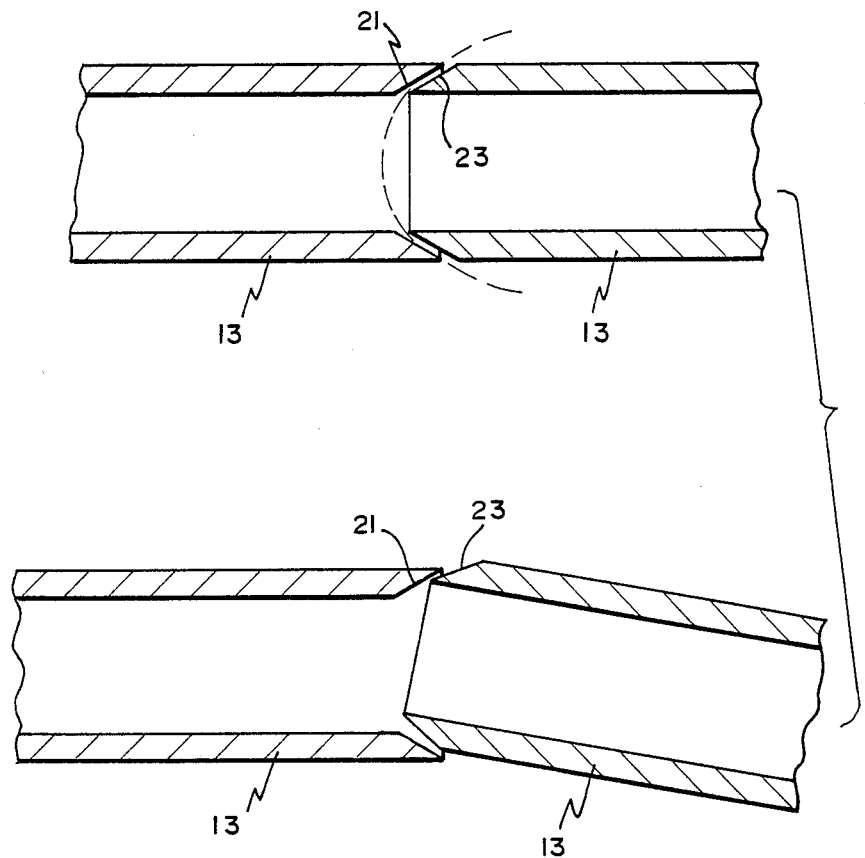
FIG. 6 is a cross sectional view of the end pieces of two adjacent rigid tubular segments in a lensguide of the invention.
Figure 7:
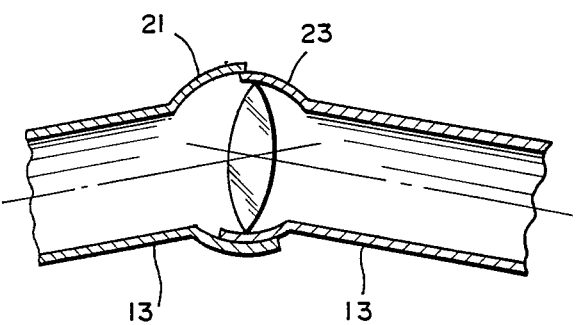
FIG. 7 is a cross sectional view of the end pieces of two adjacent rigid tubular segments in an alternative design for the lensguide of the invention.

In order for the lensguide to be flexible in all directions, it is preferred that the ends of each segment have a ball and socket structure as shown in FIGS. 6 and 7. The ball and socket joint is formed by overlapping arcuate shaped end pieces 21 and 23 which are in slidable contact with one another, permitting relative movement of adjacent segments in all radial directions. The segments are restrained from axial movement by the adjacent segments in the lensguide.

Referring again to FIG. 5, the segments 13 are preferably axially aligned and held together with the aid of plastic tubing 25. The plastic tubing may be applied as a heat shrinkable tubing which is placed in position around the series of segments and then heat shrunk to closely conform to the outer circumferences of the segments. Circumferential groove 27 serves as an anchor point for the heat shrinkable tubing. The circumferential groove results from bending the segment to form internal ridge 17. Additional grooves and ridges may be provided on the outer surface of the segments to provide further anchor points for the plastic jacket to provide a stronger bond between the jacket and segments.

As generally depicted in FIG. 8, the lensguide is attached onto the output of a laser with relatively simple connectors such as threads. Other conventional optical elements, such as beam splitters, prisms, mirrors, polarizers, and attenuaters, can be connected to the lensguide with comparably simple hardware.

As generally shown in FIG. 8, at the discharge end of the lensguide, means are provided for discharging the laser beam for surgical applications. As shown in FIGS. 9a-9b, such discharge means include (1) a simple transparent window made from ZnSe or diamond to prevent body fluids or surgical debris from entering the lensguide, (2) a convex lens made out of similar materials to either collimate or focus the beam to a diffraction limited spot at some distance from the end of the lensguide, or (3) a double lens telescope structure to either magnify or demagnify the exiting beam. In the last two cases, the outermost lens would also serve to prevent body fluids or surgical debris from entering the lensguide and interfering with its operation. The outermost surface could be continuously or periodically cleaned by a stream of flowing gas or water, saline solution, etc. transported by delivery tubes attached to the lensguide.

In addition to the $CO_2$ laser exemplified above, the lensguide of the invention provides effective beam transmission for the ultraviolet emissions of the excimer laser, thus making it suitable for a broad variety of medical applications. When an excimer laser beam passes down the length of a lensguide, it will be in a non-absorbing air space between lenses most of the time. The beam spends only a small fraction of its time in the partially absorbing lens material. If the lenses were made from pure silica and suitably anti-reflection coated, the length of a lensguide, compared to the length of a continuous silica fiber of equal attenuation would be greater by the ratio of the axial dimension of periodic air gap in the lensguide to the individual lens thickness. In effect, the excimer beam attenuation is dependent on the total path length of silica it experiences, and is not influenced by any air space it traverses. Since the ratio of the air gap to lens thickness can be made to be in the range of 5 to 10, it should be possible to increase the 1 foot propagation length in silica fibers to the range of 5 to 10 feet using the lensguide of the invention.

When silica lenses are employed for transmission of excimer laser energy, it will be practical to launch an additional lower power visible laser beam directly into the lensguide with the aid of a conventional dichroic beam combiner. The low power beam will provide a convenient "cursor" to aid the surgeon to visualize the exact location where cutting, cauterizing or vaporization will take place when the higher power excimer beam is turned on. In the case of 10.6 $\mu$m transmission, the lensguide may not be transparent to a visible "cursor" beam. In this case, single or multiple low power visible beams may be supplied by conventional optical fibers that are attached to the outer surface of the lensguide or are oriented in some way to run parallel to the lensguide. Specific techniques for accomplishing this are already quite well developed for other $CO_2$ laser beam delivery methods.

Based upon the foregoing disclosure, it should be apparent that the lensguide of the invention provides an effective means for transmitting beams from surgical lasers at wavelengths where conventional silica optical fibers are not effective. Conventional silica optical fibers are effective for wavelengths of 0.36 to 2.0 $\mu$m. At ultraviolet wavelengths less than 0.36 $\mu$m, the lensguide preferred. More specifically, in the range of 0.15 to 0.3 $\mu$m, a lensguide employing pure silica antireflection coated lenses is most preferred. Beyond 2 $\mu$m, in the infrared region, the lensguide of the invention is also more effective than silica fibers. At the 10.6 $\mu$m $CO_2$ laser wavelength, zinc sellenide (ZnSe) lenses, suitably antireflection coated are most preferred.

While the present invention has now been described in terms of certain preferred embodiments and exemplified with respect thereto, one skilled in the art will readily appreciate that various modifications, changes, omissions and substitutions may be made without departing from the spirit thereof. It is intended, therefore, that the present invention be limited solely by the scope of the following claims.

What is claimed is:

1. A surgical apparatus comprising:
   a surgical laser which emits ultraviolet or infrared radiant energy;
   a lensguide for transmitting said radiant energy from said surgical laser at a point outside a patient's body to a point on the surface or inside the patient's body, said lensguide comprising a series of spaced convex lenses disposed within a plurality of rigid tubular segments, each segment being connected end to end with an adjacent segment in such a manner as to permit bending of the lensguide; and
   means for discharging the radiant energy from said lensguide at a point inside the patient's body for performing laser surgery.

2. A surgical apparatus as claimed in claim 1, wherein said surgical laser is a $CO_2$ laser, said radiant energy is infrared radiant energy and said lenses are made from infrared transmissive material.

3. A surgical apparatus as claimed in claim 2, wherein said lenses are made from ZnSe.

4. A surgical apparatus as claimed in claim 3, wherein the surfaces of said lenses are coated with an antireflection coating with low absorption loss for the radiant energy emitted by the $CO_2$ laser.

5. A surgical apparatus as claimed in claim 1, wherein said surgical laser is an excimer laser, said radiant energy is ultraviolet radiant energy and said lenses are made from a material that is transmissive to ultraviolet radiation.

6. A surgical apparatus as claimed in claim 5, wherein said lenses are made from silica.

7. A surgical apparatus as claimed in claim 6, wherein the surfaces of said lenses are coated with an antireflection coating with low absorption loss for radiant energy emitted by the excimer laser.

8. A surgical apparatus as claimed in claim 1, wherein each rigid tubular segment contains one convex lens therein.

9. A surgical apparatus as claimed in claim 8, wherein each rigid tubular segment contains means at each end thereof for connecting with the adjacent segment in such a manner as to permit non-axial relative movement between adjacent segments.

10. A surgical apparatus as claimed in claim 9, wherein said means at each end of each rigid tubular segment comprises an arcuate shaped end piece which is in slidable, overlapping contact with the end piece of the adjacent segment, permitting relative movement of adjacent segments in all non-axial directions.

11. A surgical apparatus as claimed in claim 10, wherein said rigid tubular segments are metallic segments.

12. A surgical apparatus as claimed in claim 1, wherein said lensguide further comprises a plastic jacket surrounding said rigid tubular segments.

13. A surgical apparatus as claimed in claim 1, wherein said discharge means comprises a transparent window to prevent body fluids or surgical debris from entering the lensguide.

14. A surgical apparatus as claimed in claim 13, wherein said transparent window is made from ZnSe or diamond.

15. A surgical apparatus as claimed in claim 1, wherein said discharge means comprises a convex lens to either focus or collimate the radiant energy to a diffraction limited spot from the end of the lensguide.

16. A surgical apparatus as claimed in claim 1, wherein said discharge means comprises a double lens telescope to either magnify or demagnify the exiting radiant energy.

17. A surgical apparatus as claimed in claim 1, wherein said convex lenses are spaced so that the period of oscillation of the beam of radiant energy from said surgical laser does not coincide with an integer number of lens spacings.

18. A method of performing laser surgery, comprising emitting a beam of ultraviolet or infrared radiant energy from a surgical laser;

transmitting said beam of radiant energy through a patient's body in a lensguide comprising a series of spaced convex lenses disposed within a plurality of rigid tubular segments, each segment being connected end to end with an adjacent segment in such a manner as to permit bending of the lensguide; and discharging the beam of radiant energy from said lensguide at a point inside the patient's body for performing laser surgery.

19. The method as claimed in claim 18, wherein said beam of radiant energy is infrared radiant energy having a wavelength greater than 2 $\mu$m.

20. The method as claimed in claim 19, wherein the wavelength of said beam of infrared radiant energy is 10.6 $\mu$m.

21. The method as claimed in claim 18, wherein said beam of radiant energy is ultraviolet radiant energy having a wavelength less than 0.36 $\mu$m.

22. The method as claimed in claim 21, wherein the wavelength of said ultraviolet radiant energy is between 0.15 and 0.3 $\mu$m.

23. The method as claimed in claim 18, wherein the focal length of each lens is in the range of 2 to 20 mm.

24. The method as claimed in claim 23, wherein the focal length of each lens is in the range of 3.3 to 10 mm.

* * * * *